Figure 1:
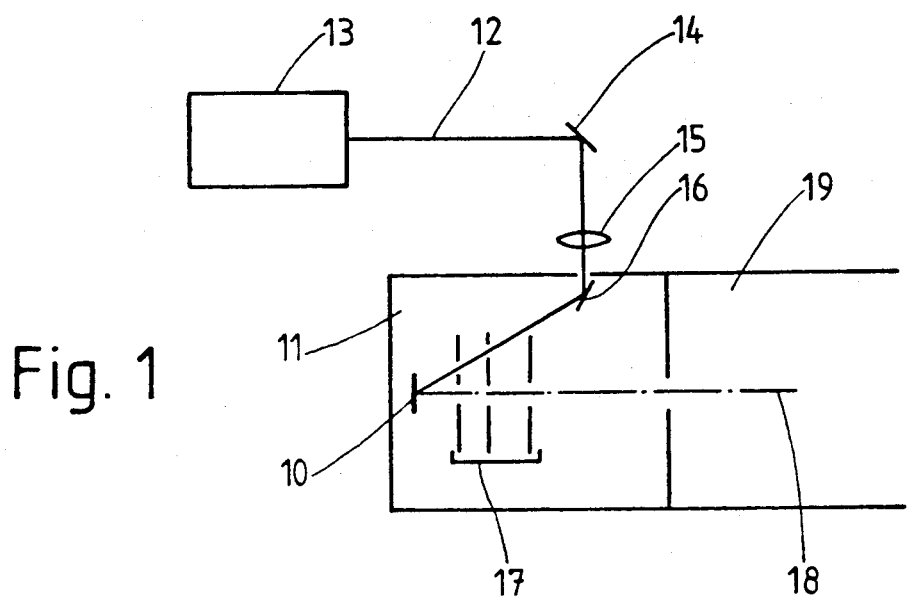

United States Patent [19]

Hillenkamp et al.

[11] Patent Number: 5,118,937
[45] Date of Patent: Jun. 2, 1992

[54] PROCESS AND DEVICE FOR THE LASER DESORPTION OF AN ANALYTE MOLECULAR IONS, ESPECIALLY OF BIOMOLECULES

[75] Inventors: Franz Hillenkamp; Michael Karas, both of Münster; Ulrich Giessmann, Bremen, all of Fed. Rep. of Germany

[73] Assignee: Finnigan MAT GmbH, Bremen, Fed. Rep. of Germany

[21] Appl. No.: 570,283

[22] Filed: Aug. 21, 1990

[30] Foreign Application Priority Data

| Aug. 22, 1989 | [DE] | Fed. Rep. of Germany | 3927602 |
| Aug. 22, 1989 | [DE] | Fed. Rep. of Germany | 3927603 |
| Sep. 20, 1989 | [DE] | Fed. Rep. of Germany | 3931288 |
| Nov. 8, 1989 | [DE] | Fed. Rep. of Germany | 3937165 |
| Jun. 10, 1990 | [DE] | Fed. Rep. of Germany | 4017804 |

[51] Int. Cl.⁵ .................... B01D 59/44; H01J 49/00
[52] U.S. Cl. .................... 250/282; 250/288; 250/423 P
[58] Field of Search .................... 250/282, 288, 423 P

[56] References Cited

U.S. PATENT DOCUMENTS

| 4,208,585 | 6/1980 | Vogt | 250/288 |
| 4,259,572 | 3/1981 | Brunnee et al. | 250/288 |
| 4,296,322 | 10/1981 | Wechsung | 250/423 P |
| 4,330,208 | 5/1982 | Eloy | 250/288 |
| 4,468,468 | 8/1984 | Benninghoven et al. | 250/288 |
| 4,733,073 | 3/1988 | Becker et al. | 250/288 |
| 4,740,692 | 4/1988 | Yamamoto et al. | 250/288 |
| 4,920,264 | 4/1990 | Becker | 250/282 |
| 4,988,879 | 1/1991 | Zare et al. | 250/288 |

FOREIGN PATENT DOCUMENTS 2141387 2/1973 Fed. Rep. of Germany.

OTHER PUBLICATIONS

"Liquid Chromatographic Assay for the Measurement of Glucuronidation of Arylcarboxylic Acids Using Uridine Diphospho-[U-$^{14}$C]Glucuronic Acid", Hansen et al., *Journal Chromatogra Biomed. Appl.*, 1986, 383(1) pp. 51–60.

Primary Examiner—Bruce C. Anderson
Attorney, Agent, or Firm—Flehr, Hohbach, Test, Albritton & Herbert

[57] ABSTRACT

The invention relates to a process for the laser desorption of analyte molecular ions, especially of biomolecules, from a specimen. The object of the invention is to improve a process of this type in such a way that intact desorption of biomolecules, preferably of large molecular mass, is also possible with a laser. This is achieved by using laser light of a wavelength of about 300 nm or greater than 300 nm and using a matrix which is able to absorb in the selected wavelength range.

34 Claims, 2 Drawing Sheets

PROCESS AND DEVICE FOR THE LASER DESORPTION OF AN ANALYTE MOLECULAR IONS, ESPECIALLY OF BIOMOLECULES

DESCRIPTION

The invention relates to a process for the laser desorption of analyte molecular ions, especially of biomolecules, preferably with a molecular mass in the range from 10,000 to several hundred thousand dalton, from a specimen which contains the analyte and a matrix which absorbs laser light. The invention also relates to a device for carrying out the process.

Matrix-assisted laser desorption is known as such per se, specifically in the UV range, especially at a wavelength of 266 nm.

However, experience to date with ultraviolet laser desorption has shown that intact molecular ions, especially of biomolecules, can be desorbed from a specimen only with great difficulty or not at all, because the analyte molecules also absorb laser light, which may result in damage thereto.

Hence the object of the invention is to improve the abovementioned process in such a way that even biomolecular ions, preferably with molecular masses greater than 10,000 dalton, can be desorbed intact from a specimen by means of laser desorption.

The object is achieved according to the invention by using laser light with a wavelength greater than or equal to 300 nm and a matrix which is able to absorb in the selected wavelength range, the laser light used being either in the long wavelength UV range or the IR range.

To date, Nd-YAG lasers with a wavelength of about 266 nm have mostly been used for laser desorption because, particularly for this wavelength, a large number of matrices which are able to absorb this wavelength is available. However, biomolecules are, in particular, also able to absorb in this wavelength range, so that it is frequently impossible to desorb intact biomolecules with a laser of this type.

Most biomolecules no longer absorb laser light in the wavelength range greater than or equal to 300 nm proposed according to the invention, so that the desorption of intact biomolecules is possible and advantageous with a suitable matrix which is able to absorb in this wavelength range. There are only very few biomolecules which absorb wavelengths above 300 nm, for example blood pigment. However, these biomolecules tend to be exceptions.

Suitable matrices for the wavelength ranges according to the invention are evident from Tables 1 and 2, and independent protection is claimed for these matrices according to the invention.

TABLE 1

Selected matrices for UV laser desorption/ionization

| Matrix | Wavelength | Structural formula |
|---|---|---|
| Nicotinic acid | 266–290 nm | (pyridine ring with COOH) |
| Benzoic acid derivatives (2,5-dihydroxybenzoic acid, aminobenzoic acid) | 266, 377, 355 nm | (benzene ring with COOH, X, Y) |
| Pyrazinecarboxylic acid | 266 nm | (pyrazine ring with COOH) |
| 3-amino-2-carboxypyrazine | 337 nm | |
| Vanillic acid | 266 nm | (benzene ring with CH$_3$O, HO, COOH) |
| Cinnamic acid derivatives (ferulic acid, sinapinic acid, caffeic acid) | 266, 337, 355 nm | H—C=CH—COOH (benzene ring with X, Y, Z) |

TABLE 1-continued

| Selected matrices for UV laser desorption/ionization | | |
|---|---|---|
| Matrix | Wavelength | Structural formula |
| 3-Nitrobenzyl alcohol | 266 nm | 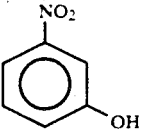 |

TABLE 2

Selected matrices for infrared (2.94 μm) laser desorption/ionization

All matrices which have been found to be suitable for UV LDI (Mono-, di-, tri-) carboxylic acids: R—COOH e.g.
- maleic acid
- malonic acid
- succinic acid
- lactic acid liquid matrices
- glycerol
- triethanolamine
- carbamide (urea)

An additional point to be taken into account with these suitable matrices is that not only must the particular matrix be able to absorb in the selected wavelength range or at the selected wavelength in each case, it being increasingly difficult in principle to find small molecules with high absorption as the wavelength increases, for reasons of the electronic molecular structure, but also that other properties, which are by no means obvious, also contribute to the utilizability of a suitable absorbing matrix. These include, on the one hand, the necessity for matrix molecules to form a homogeneous mixture with the analyte molecules, even on evaporation of the solvent on introduction of the sample or the specimen into the vacuum, and not to segregate. On the other hand, the matrix molecules act as proton donors from the electronically excited state and thereby make the ionization of the analyte molecules possible in the first place. Neither property can be found in customary sets of tables. An example which may be used to show the difficulty of finding suitable molecules is that, for example, 3-pyridinecarboxylic acid (nicotinic acid) is an excellent matrix at 266 nm, whereas 2- and 4-pyridinecarboxylic acids, in which the COOH group is merely moved to a different position on the ring, are completely useless as matrix.

The fact that the molecules have to be not only desorbed but also ionized makes it surprising that wavelengths from the IR range are also suitable according to the invention for a laser desorption of this type. To date it has generally been assumed in the literature that a thermal process is the cause of the ionization of the molecules. On this basis, the possibility of carrying out a desorption of large, thermally labile ions with IR wavelengths must have tended to be regarded as improbable.

It has emerged that O—H and N—H groups are also advantageously among the particularly strong absorbers in the wavelength range according to the invention. However, at the same time, these groups are the groups which form the chemical linkage between analyte and matrix. Preferential irradiation into these linkages results in improved liberation of the analyte molecules, demonstrated by signal strengths which are all higher than with the known UV desorption. At the same time, a proton transfer may be associated with the breakage of these linkages and increases the yield of charged analyte molecules.

Water as the matrix readily evaporates in a vacuum, so that when water is used this undesired vaporization should be suppressed where possible, for example by shock-cooling of the sample and insertion of the cooled, frozen sample into the vacuum.

The changeover from the known UV desorption to the IR desorption according to the invention has the particular advantage moreover that there is a considerably wider selection of suitable liquid matrices. The result of this is, in particular, that coupling of liquid chromatography and mass spectrometry is also possible according to the invention. Independent protection is also claimed for this coupling.

Another development of the process according to the invention, for which independent protection is likewise claimed, is distinguished in that the chosen combination of wavelength and matrix is such that the number of charges on the ions generated is higher.

This has the particular advantage that such ions with many charges can be detected, for example, also in classical mass spectrometers, that is to say, for example, not in time-of-flight mass spectrometers, which, by reason of their design, are really suitable only for smaller molecules. This is possible because, for example, an ion with a mass of 100,000 dalton and with ten charges behaves in a mass spectrometer exactly like an ion with a mass of 10,000 dalton and with only one charge.

Ions with multiple charges can also, moreover, be easily fragmented by impact with other particles or with surfaces or by photon bombardment. This is of great importance and a great advantage in particular for the so-called MS—MS technique in which two mass spectrometers are arranged in series. This makes possible particularly satisfactory research into the structure of molecules.

It is also possible, for the specific generation of multiply charged ions, to alter the pulse duration, the irradiance and/or the size of the irradiated area.

Another development of the process according to the invention provides for transillumination of the specimen (from behind) with the laser light, for which purpose the substrate or a support for the specimen is transparent to the appropriate wavelength. This transillumination (back illumination) is particularly advantageous especially in the case of coupling of liquid chromatography and mass spectrometry.

A device according to the invention, preferably for carrying out the process according to the invention, is distinguished by a laser for laser light with a wavelength greater than or equal to 300 nm, possibilities being a UV laser or an IR laser.

For example, it is possible to employ nitrogen lasers, $CO_2$ lasers and Er lasers, which in each case emit laser light with a wavelength of about 337 nm, 10,600 nm and 3,000 nm respectively.

It is possible according to the invention to use Er lasers with different crystal materials, for example Er-YAG lasers or Er-YILF lasers. The wavelength of this Er laser varies somewhat depending on the crystal material so that this makes fine adjustment of Er lasers possible virtually in a larger wavelength range.

The use of HF lasers or Ho-YAG lasers, for example, is also conceivable according to the invention.

The use of a laser with a wavelength greater than or equal to 300 nm additionally permits the advantageous use of a light guide, for example an optical fibre, for guiding the laser light from the laser to the specimen.

The use of light guides advantageously permits a particularly simple design and operation of the device according to the invention, in particular the light guides can be inserted in a particularly straightforward manner into a vacuum, and it is possible with the light guide to adjust in a straightforward manner the desired angle of incidence of the light on the specimen, in particular without the need to change the orientation of the laser itself or of the specimen at all.

Figure 2:
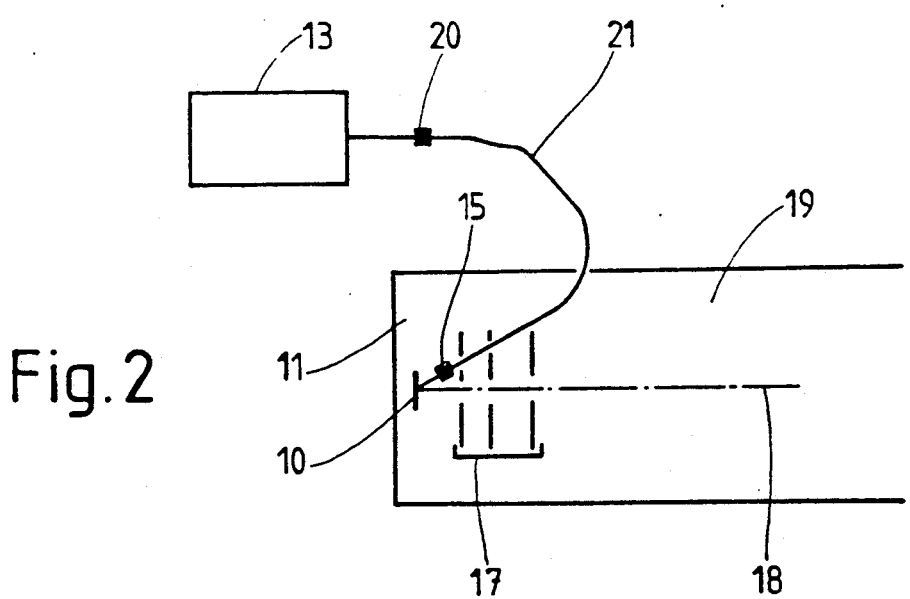
Figure 3:
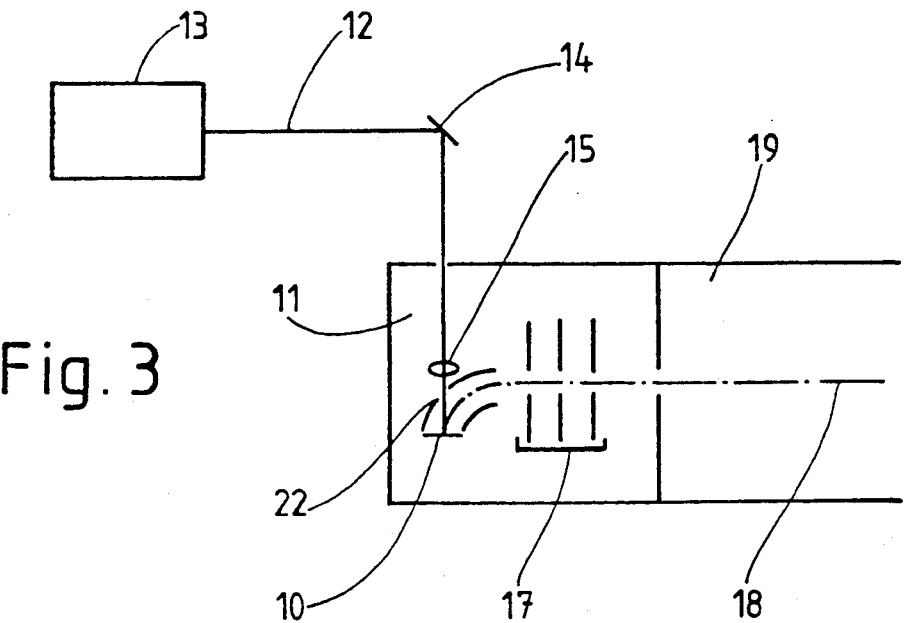
Figure 4:
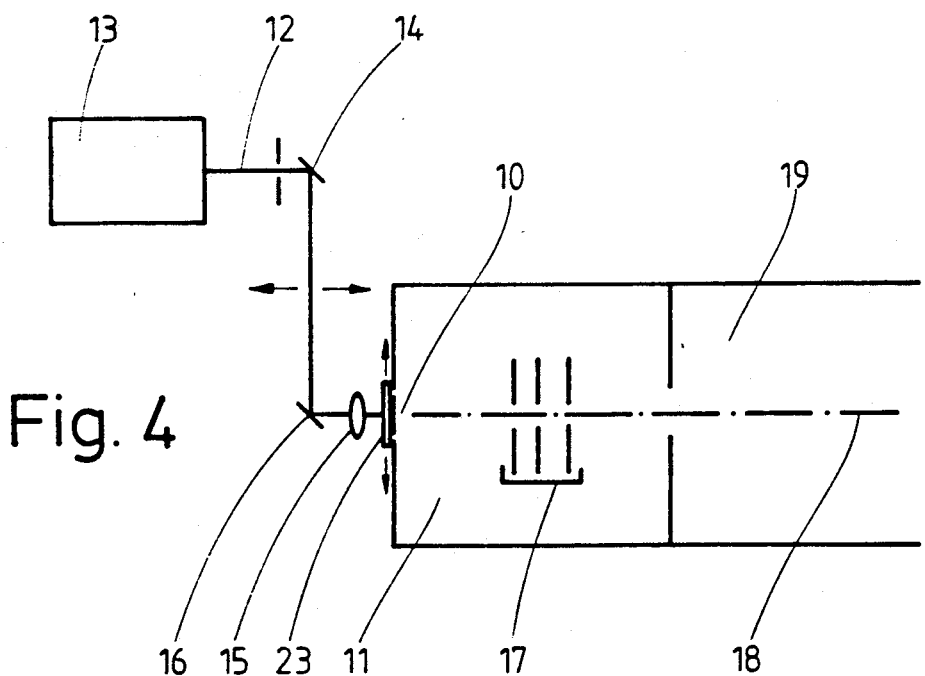

Exemplary embodiments from which further inventive features emerge are depicted in the drawing. The diagrams show in:

FIG. 1 a plan view of a first exemplary embodiment of a device for laser desorption, FIG. 2 a plan view of a second exemplary embodiment of a device for laser desorption, FIG. 3 a plan view of a third exemplary embodiment of a device for laser desorption and FIG. 4 a fourth exemplary embodiment of a device for laser desorption.

FIG. 1 shows a first exemplary embodiment of a device for the laser desorption of analyte molecules or of their ions from a specimen. The specimen is located on a specimen support 10 which is arranged in the vacuum chamber of an ion source 11. The specimen support 10 acts as target for a laser beam 12 which is emitted by a laser 13. The laser beam 12 consists of laser light, for example ultraviolet laser light, of a wavelength greater than or equal to 300 nm. The laser 13 can be, for example, a nitrogen laser with laser light of wavelength 337 nm. It is also possible to use, for example, carbon dioxide lasers with laser light of wavelength 10,600 nm or Er-YAG lasers with laser light of wavelength 3,000 nm.

The laser beam 12 is in this first exemplary embodiment deflected by about 90°, by means of a reflecting mirror 14, in order to align the laser beam 12, and is then focused by means of a lens 15. After the laser beam 12 has entered the vacuum chamber of the ion source 11, the laser beam 12 is deflected a second time, with a second reflecting mirror 16, in such a way that it impinges on the specimen support 10, and thus on the specimen, at an angle about 25° to 45° to the normal to the surface.

Analyte ions are desorbed by the laser beam 12 at the site of the specimen and are extracted by means of an ion-optical system 17 and focused to an ion beam 18.

The ion beam 18 enters the vacuum chamber 19 of an analyzer which is connected to the vacuum chamber of the ion source 11. The analyzer can be, for example, a mass spectrometer.

FIG. 2 shows a second exemplary embodiment of a device for the laser desorption of analyte molecules.

The same components are identified in FIGS. 2 and 3 with the same reference numbers as in FIG. 1.

In this exemplary embodiment, the laser beam 12 of the laser 13 is not deflected with reflecting mirrors, on the contrary a light guide 21 (an optical fibre) is connected optically to the laser 13 by a beam feed-in 20 and is used to guide the laser beam. A beam feed-out at the end of the light guide 21 forms a focusing lens 15.

Laser light with a wavelength greater than or equal to 300 nm should preferably be used so that the laser light from the laser 13 can be guided as well as possible by the light guide 21.

The light guide 21 can be inserted in a particularly straightforward manner into the vacuum of the ion source 11, and its operation is particularly easy, and the desired beam angle of the laser light with respect to the normal to the surface of the specimen support 10 can be adjusted in a straightforward manner, in particular without deflecting mirrors 14, 16, because the light guide 21 is flexible.

FIG. 3 depicts a third exemplary embodiment of a device for the laser desorption of analyte molecules.

The device in FIG. 3 once again shows, similar to the device in FIG. 1, a reflecting mirror 14 for deflecting the laser beam 12. However, in the exemplary embodiment in FIG. 3, the specimen support 10 is arranged in the ion source 11 in an orientation such that the laser beam 12 after the deflection by the reflecting mirror 14 impinges at right angles (along the normal to the surface) on the specimen support 10 after it has been focused by a focusing lens 15. In the exemplary embodiment in FIG. 3, this focusing lens 15 is located, in contrast to the exemplary embodiment of FIG. 1 and similar to the exemplary embodiment in FIG. 2, inside the vacuum chamber of the ion source 11.

Since the orientation of the specimen support 10 in the ion source 11 is different in the exemplary embodiment in FIG. 3 from that in the preceding exemplary embodiments, the ion source 11 has, in addition to the ion-optical system 17 a deflector unit 22 which deflects the generated ion beam 18 into the desired ray direction through the ion-optical system 17. The deflector unit preferably functions electrostatically. For example, the deflector unit 22 can be a simple deflecting condenser.

The laser 13 used in all the exemplary embodiments emits laser light with a wavelength greater than or equal to 300 nm. In addition to the advantage relating to the intact desorption of biomolecules, a laser 13 of this type has the further advantage that its cost is lower than, for example, a Nd-YAG laser with laser light of wavelength 266 nm which is mostly used otherwise.

FIG. 4 shows a fourth exemplary embodiment of a device for laser desorption. The same components in this FIG. 4 are identified with the same reference numbers as in the preceding figures.

FIG. 4 shows, in particular, a transparent sample support 23 for the sample 10 or specimen support 10. Thus, in this exemplary embodiment, the sample is transilluminated from behind. The transparent sample support 23 can in this case act as vacuum support.

A transillumination of this type according to the invention, also called back illumination, is advantageous especially when mass spectrometry is coupled to liquid chromatography, especially when a liquid chromatography specimen is to be analyzed by mass spectrometry.

We claim:

1. Process for the laser desorption of analyte molecular ions of biomolecules comprising the steps of locating a specimen in a range from 10,000 to several hundred thousand Dalton, providing a matrix for said analyte which absorbs laser light, and irradiating said specimen with laser light with a wavelength of about 300 nm or greater, said matrix being able to absorb said laser light.

2. Process according to claim 1, characterized in that laser light with a wavelength in the infrared spectral range is used.

3. Process according to claim 2, characterized in that a $CO_2$ laser is employed as laser.

4. Process according to claim 2, characterized in that an Er laser is employed as laser.

5. Process according to claim 4, characterized in that an Er-YAG laser is employed.

6. Process according to claim 4, characterized in that an Er-YILF laser is employed.

7. Process according to claim 2, characterized in that a nitrogen laser is employed as laser.

8. Process according to claim 1 characterized in that a benzoic acid derivative, for example aminobenzoic acid or 2,5-dihydroxybenzoic acid, is used as matrix.

9. Process according to claim 1 characterized in that a nicotinic acid derivative, preferably hydroxy-aminonicotinic acid, is used as matrix.

10. Process according to claim 1 characterized in that a pryrazinecarboxylic acid derivative, preferably 3-aminopryazione-2-carboxylic acid, is used as matric.

11. Process according to claim 1 characterized in that water, preferably in the solid phase, is used as matrix.

12. Process according to claim 1 characterized in that a carboxylic acid or a carboxylic acid derivative is used as matrix.

13. Process according to claim 1 characterized in that glycerin or glycerol is used as matrix.

14. Process according to claim 1 characterized in that urea is used as matrix.

15. Process according to claim 1 characterized in that triethanolamine is used as matrix.

16. Process according to claim 1 characterized in that a liquid matrix is used.

17. Process for the laser desorption of analyte molecular ions, according to claim 16, characterized in that the laser desorption is coupled to liquid chromatography.

18. Process according to claim 17, characterized in that a direct sequence is carried out.

19. Process according to claim 1 characterized in that the laser light irradiation of the specimen takes place through a substrate or support each of which is transparent to the selected light.

20. Process according to claim 1 characterized in that a laser wavelength and a matrix are selected and assigned to one another or combined with one another and, in the interaction thereof, lead to a laser desorption of ions of a higher charge number.

21. Process according to claim 20, characterized in that ions with more than one charge are generated in larger number than those with only one charge.

22. Process according to claim 20, characterized in that ions with more than one charge per 10,000 Dalton molecular mass are generated.

23. Process according to claim 22 characterized int hat the pulse duration, irradiance on the specimen and/or the size of the irradiated area on the specimen are employed or used as changeable parameters in the generation of the multiply charged ions.

24. Process according to claim 23, characterized in that the multiply charged ions are detected in a mass spectrometer whose upper limit of detectable singly charged ions is below the mass of the molecules to be detected.

25. Process according to claim 22, characterized in that the multiply charged ions are fragmented in a mass spectrometer by impact with other particles (CID), with a surface (SID), or by photon irradiation, are analyzed in another mass spectrometer (MS—MS).

26. Process according to claim 20 characterized in that a combination of caffeic or succinic acid is used as matrix and a wavelength in the infrared range is used, the wavelength of an Er or CO2 laser.

27. Device for the laser desorption of analyte molecular ions, of biomolecules, with a molecular mass in the range from 10,000 to several hundred thousand Dalton, from a specimen which contains the analyte comprising a laser for producing light of a wavelength of about 300 nm or greater, said biomolecules not absorbing said laser light; and a matrix for said analyte which absorbs said laser light.

28. Device according to claim 27, characterized in that the laser (13) is a UV laser.

29. Device according to claim 28, characterized in that the laser (13) is a nitrogen laser with laser light of a wavelength of about 337 nm.

30. Device according to claim 27, characterized in that the laser (13) is a IR laser.

31. Device according to claim 30, characterized in that the laser (13) is a $CO_2$ laser with laser light of a wavelength of about 10,600 nm.

32. Device according to claim 30, characterized in that the laser (13) is an Er laser.

33. Device according to claim 32, characterized in that the laser (13) is an Er-YAG laser with laser light of a wavelength of about 3,000 nm or an Er-YILF laser or Er laser with a different crystal material.

34. Device according to claim 27, characterized by a light guide (21) which is optically connected to the laser (13) for guiding the laser light.

* * * * *